(12) United States Patent
Probst et al.

(10) Patent No.: US 7,103,415 B2
(45) Date of Patent: Sep. 5, 2006

(54) CONTOURED HOUSING FOR AN IMPLANTABLE MEDICAL DEVICE

(75) Inventors: Joseph M. Probst, Williamsville, NY (US); Philip S. Wutz, Williamsville, NY (US)

(73) Assignee: Wilson Greatbatch Technologies, Inc., Clarence, NY (US)

( * ) Notice: Subject to any disclaimer, the term of this patent is extended or adjusted under 35 U.S.C. 154(b) by 492 days.

(21) Appl. No.: 10/199,773

(22) Filed: Jul. 19, 2002

(65) Prior Publication Data

US 2003/0017372 A1    Jan. 23, 2003

Related U.S. Application Data

(60) Provisional application No. 60/306,647, filed on Jul. 19, 2001.

(51) Int. Cl.
*A61N 1/372* (2006.01)

(52) U.S. Cl. ............................................ 607/36
(58) Field of Classification Search ........... 607/1–2, 607/36
See application file for complete search history.

(56) References Cited

U.S. PATENT DOCUMENTS

| | | | |
|---|---|---|---|
| 906,644 A | 12/1908 | Meade | |
| 1,402,591 A | 1/1922 | Gallus | |
| 2,861,117 A | 11/1958 | Sindel et al. | |
| 3,897,265 A | 7/1975 | Jaggard | |
| 3,987,799 A * | 10/1976 | Purdy et al. | 607/36 |
| 4,014,346 A * | 3/1977 | Brownlee et al. | 607/33 |
| 4,057,068 A * | 11/1977 | Comben | 607/36 |
| 4,094,321 A * | 6/1978 | Muto | 607/36 |
| 4,157,720 A * | 6/1979 | Greatbatch | 607/36 |
| 4,243,042 A * | 1/1981 | Ware | 607/36 |
| 4,314,562 A * | 2/1982 | Ware | 607/36 |
| 4,361,153 A * | 11/1982 | Slocum et al. | 607/32 |
| 4,659,636 A | 4/1987 | Suzuki et al. | |
| 4,785,827 A * | 11/1988 | Fischer | 607/57 |
| 4,894,295 A | 1/1990 | Cheiky | |
| 5,240,788 A | 8/1993 | Eales | |
| 5,270,133 A | 12/1993 | Baumann, III | |
| 5,288,565 A | 2/1994 | Gruenstern | |
| 5,326,652 A | 7/1994 | Lake | |
| 5,370,669 A * | 12/1994 | Daglow et al. | 607/36 |
| 5,411,539 A * | 5/1995 | Neisz | 607/36 |
| 5,439,482 A * | 8/1995 | Adams et al. | 607/5 |
| 5,486,215 A | 1/1996 | Kelm et al. | |
| 5,486,431 A | 1/1996 | Tuttle et al. | |
| 5,549,717 A | 8/1996 | Takeuchi et al. | |
| 5,556,722 A | 9/1996 | Narukawa et al. | |
| 5,603,737 A | 2/1997 | Marincic et al. | |
| 5,629,107 A | 5/1997 | Shioda et al. | |
| 5,674,259 A * | 10/1997 | Gray | 607/20 |

(Continued)

FOREIGN PATENT DOCUMENTS

EP    0 202 857 B1    5/1986

(Continued)

*Primary Examiner*—Robert E. Pezzuto
*Assistant Examiner*—Kristen Mullen
(74) *Attorney, Agent, or Firm*—Michael F. Scalise (57) ABSTRACT

An implantable medical device having opposed major sidewalls of contoured shape closely fits the curved shape of a body. The contoured major sidewalls can have a curved shape of a continuous radius with the major sidewalls deflecting in a similar direction. Alternatively, the major sidewalls can have a curved shape corresponding to more than one radius. The device housing is either deep drawn or includes two clam shells that are secured together.

52 Claims, 7 Drawing Sheets

U.S. PATENT DOCUMENTS

| | | |
|---|---|---|
| 5,716,728 A | 2/1998 | Smesko et al. |
| 5,776,169 A | 7/1998 | Schroeppel |
| 5,895,414 A * | 4/1999 | Sanchez-Zambrano ....... 607/36 |
| 5,926,362 A | 7/1999 | Muffoletto et al. |
| 5,958,088 A | 9/1999 | Vu et al. |
| 6,004,693 A | 12/1999 | Fukuda et al. |
| 6,040,084 A | 3/2000 | Kurasawa et al. |
| 6,048,642 A | 4/2000 | Woolsey |
| 6,176,879 B1 * | 1/2001 | Reischl et al. ........... 623/11.11 |
| 6,265,102 B1 | 7/2001 | Shrim et al. |
| 6,334,879 B1 | 1/2002 | Muffoletto et al. |
| 6,445,948 B1 | 9/2002 | Somdahl et al. |
| 6,445,956 B1 * | 9/2002 | Laird et al. .................... 607/61 |
| 6,498,951 B1 | 12/2002 | Larson et al. |
| 6,721,597 B1 * | 4/2004 | Bardy et al. .................... 607/4 |
| 2001/0049057 A1 | 12/2001 | Frustaci et al. |
| 2003/0040781 A1 | 2/2003 | Larson et al. |

FOREIGN PATENT DOCUMENTS

| | | |
|---|---|---|
| EP | 0 928 035 A1 | 7/1999 |
| GB | 1 468 120 | 10/1975 |
| GB | 2 137 801 A | 10/1984 |
| JP | 06181069 | 6/1994 |
| JP | 10199493 | 7/1998 |
| WO | WO 95/06958 | 3/1995 |
| WO | WO 97/38455 | 10/1997 |
| WO | WO 01/82393 A2 | 11/2001 |

* cited by examiner

CONTOURED HOUSING FOR AN IMPLANTABLE MEDICAL DEVICE

CROSS-REFERENCE TO RELATED APPLICATION

This application claims priority based on provisional application Serial No. 60/306,647, filed Jul. 19, 2001.

BACKGROUND OF THE INVENTION

The present invention relates to implantable medical devices and, more particularly, to housings for implantable medical devices. The housings have contoured surfaces to more closely conform to body contours. This facilitates implantation in areas of a body that were heretofore not possible because of geometrical limitations.

SUMMARY OF THE INVENTION

Implantable medical devices include hearing-assist devices, artificial hearts, neurostimulators, drug pumps, cardiac pacemakers, cardiac defibrillators and heart-assist devices. Conventionally, these devices include a housing with planar side walls, such as in a prismatic design. However, the shape of the housing limits the areas in a body, human or otherwise, in which the device can be implanted. If an area of the body, such as the skull, must be excavated, a conventional prismatic housing requires that the cavity be shaped to fit the planar prismatic design. This may necessitate more excavation than is required if the housing is contoured to fit the patient's anatomy. Furthermore, the planar design of current prismatic housings makes it more difficult for implantable devices to be placed in other locations in the body such as the arms and legs.

Accordingly, there is a need for a housing for an implantable medical device that is shaped or contoured to more closely fit the curved shape of a body. This facilitates implanting assist devices in areas where it is difficult, if not impossible, to place conventionally shaped devices. Furthermore, not only does a contoured shaped housing aid in the placement of assist devices into the body where they could not previously be placed, but it also helps in placing them in areas of the body where they are frequently used, but without undo excavation.

These and other advantages of the present invention will become increasingly more apparent to those of ordinary skill in the art by reference to the following description together with the appended drawings.

DETAILED DESCRIPTION OF THE PREFERRED EMBODIMENTS

Figure 1:
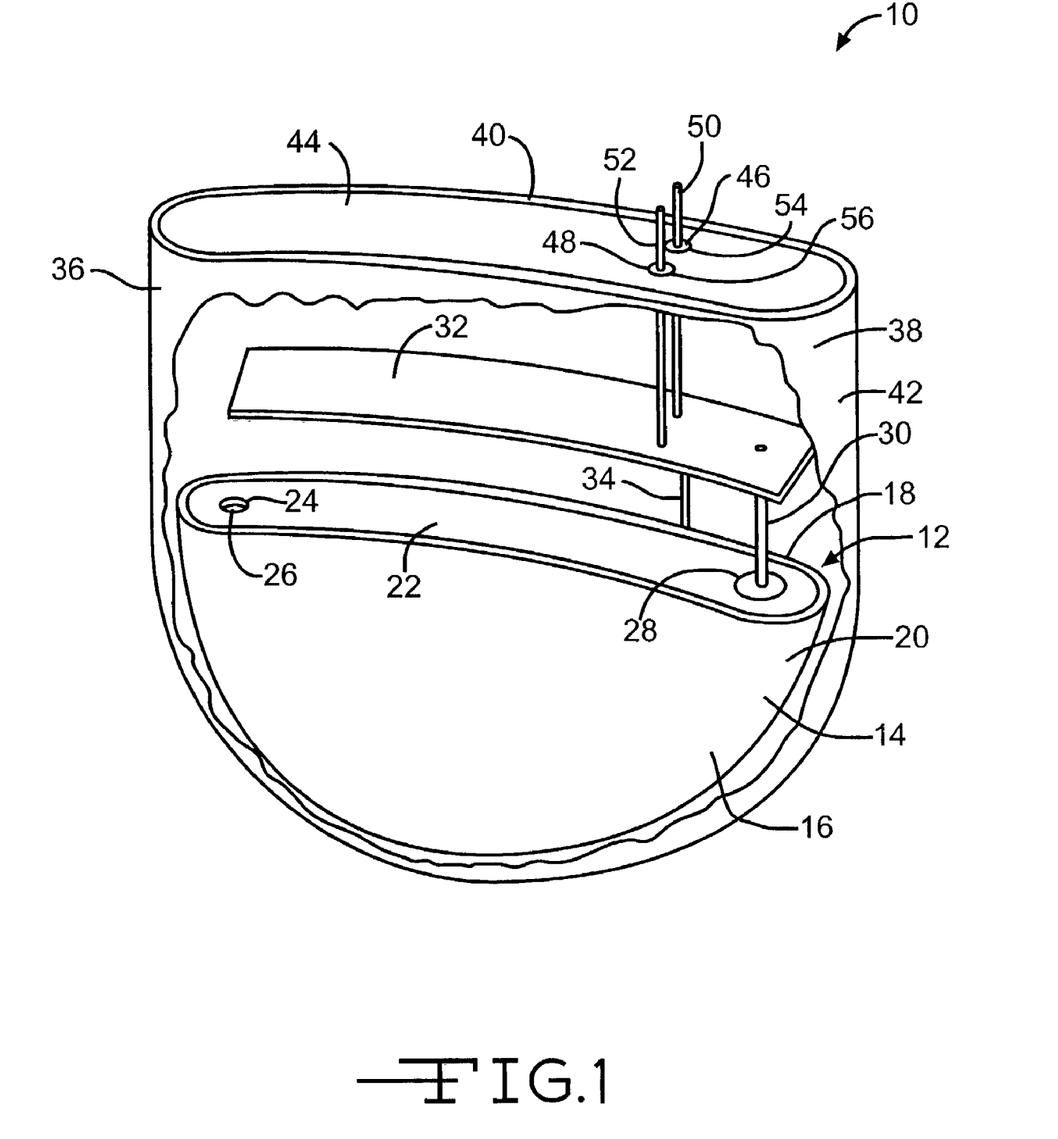
FIG. 1 is an elevational view, partly broken away, of an implantable medical device 10 comprised of a contoured housing 36 with a power source 12 of a contoured casing 14 housed therein.

FIG. 1 shows a representative implantable device 10 powered by an implantable electrochemical cell 12. Both the device 10 and the cell 12 are comprised of housings or casings having contoured side walls according to the present invention The housings and casings of this invention are preferably of conductive materials selected from nickel, aluminum, stainless steel, mild steel, tantalum and titanium.

The cell 12 is comprised of a casing 14 having spaced apart and opposed major front and back side walls 16 and 18. The walls 16, 18 each have a generally semicircular shape with a planar upper edge. The side walls 16, 18 extend to and meet with a semicircular intermediate end wall 20 that curves to meet them along their entire radial perimeter. The side walls 16, 18 and end wall 20 form the casing as a unitary, deep drawn member. Both of the major front and back side walls 16, 18 have a curved shape of a continuous radius deflecting in a similar direction and extending from the end wall 20.

The side walls and end wall of the deep drawn casing 14 form an opening closed by a lid 22. The lid also includes an electrolyte fill opening 24 closed by ball 26 and a terminal pin opening supporting a ring of insulation glass 28 surrounding a terminal pin 30 for one of the anode and the cathode electrodes of the cell. The casing 14 serves as the terminal for the other electrode. For a more detailed description of this type of cell, reference is made to U.S. Pat. No. 5,905,001 to Elliott et al., which is assigned to the assignee to the present invention and incorporated herein by reference.

The electrochemical cell 12 serves as the power supply for the control circuitry 32 of the implantable device 10. Lead 34, connected to the casing 14, and terminal pin 30 provides electrical power from the cell to the control circuitry. There may also be a capacitor (not shown) inside the casing for a medical device such as a cardiac defibrillator.

The implantable device 10 includes a housing 36 having spaced apart and opposed major front and back side walls 38 and 40. The walls 38, 40 each have a generally semicircular shape with a planar upper edge. The walls 38, 40 extend to and meet with a semicircular intermediate end wall 42 that curves to meet them along their entire radial perimeter. The side walls 38, 40 and end wall 42 form the housing 36 as a unitary, deep drawn member. Both the front and back major side walls 38, 40 have a curved shape of a continuous radius deflecting in a similar direction and extending from the end wall 42.

The side walls and end wall of the deep drawn housing 36 form an opening closed by a lid 44. The lid 44 comprises two openings 46 and 48 through which respective feedthrough wires 50 and 52 pass. The feedthrough wires extend from a distal end positioned inside the housing 36 connected to the control circuitry 32 for the medical device 10 to proximal ends for connection to leads (not shown). The leads connect the medical device to the body being assisted. The feedthrough wires 50 and 52 are electrically insulated from the lid 44 by respective ceramic-to-metal seals or glass-to-metal seals 54 and 56.

In that manner, the device 10 is implantable into areas of the body which may not have been considered before with devices having more prismatic shapes with rectangular cross-sections. Also, the implantable device 10 more closely conforms to the contours of a body so that when it is used to assist a person, there may be less excavation required than is currently needed with conventionally shaped devices.

Turning to FIGS. 2A, 2B, 3A, 3B and 4, these drawings show other representative shapes for deep drawn medical device housings 60, 100 and 140 according to the present invention.

Figures 2A, 2B:
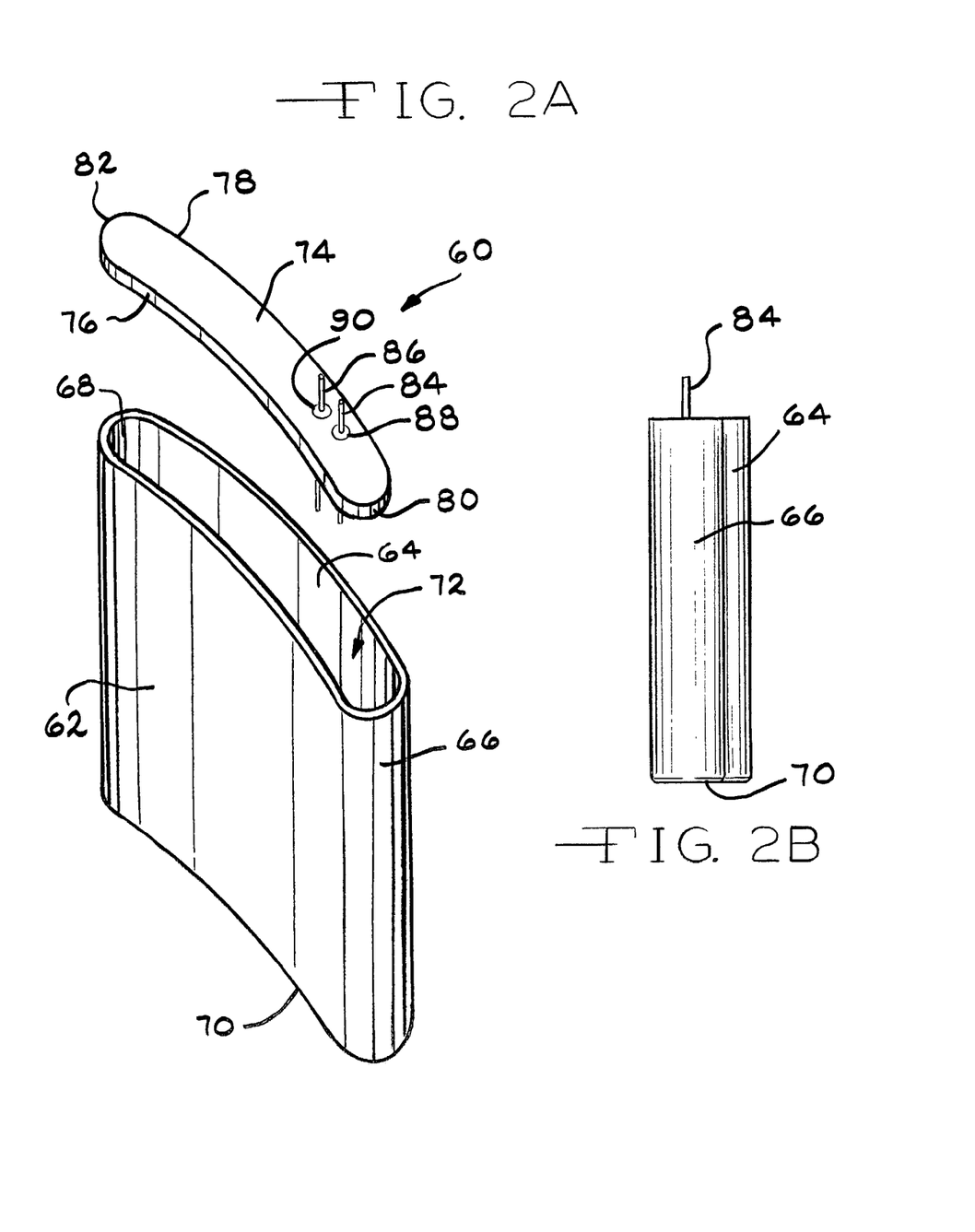
FIG. 2A is an exploded view of one embodiment of a contoured deep drawn cell housing 30 according to the present invention.
FIG. 2B is a side elevational view of the housing 30 shown in FIG. 2A.

The housing 60 illustrated in FIGS. 2A and 2B includes spaced apart and opposed major front and back side walls 62 and 64 extending to and meeting with curved right and left end walls 66 and 68. The side walls 62, 64 and end walls 66, 68 are connected to a planar bottom wall 70 forming the housing as a unitary, deep drawn member. Both of the major front and back side walls 62, 64 have a curved shape of a continuous radius deflecting in a similar direction and extending from the right and left end walls 66, 68. The curvatures of the front and back side walls 62, 64 are the same, although that is not necessary. As will be described in detail hereinafter, in some housing designs it may be beneficial to provide one or the other of the front and back side walls having a greater curvature than the other. For example, it may be useful to provide the front wall 62 with a greater curvature than the back wall 64. This would optimize internal volume while maintaining housing curvature for implantation purposes, and the like.

The side walls and end walls of the deep drawn housing 60 form an opening 72 closed by a generally planar lid 74. Lid 74 has a peripheral shape matching that of the opening 72 and formed of a concave edge 76 opposite a convex edge 78, both of which extend to and meet with curved right and left edges 80 and 82. That way, when the lid 74 is secured to the upper edges of the housing side walls and end walls, the opening 72 is closed in a hermetic manner.

The lid 74 includes feedthrough wires 84 and 86 for connection to the body being assisted. The feedthrough wires 84, 86 are insulated from the lid by respective glass or ceramic seals 88, 90.

Figures 3A, 3B:
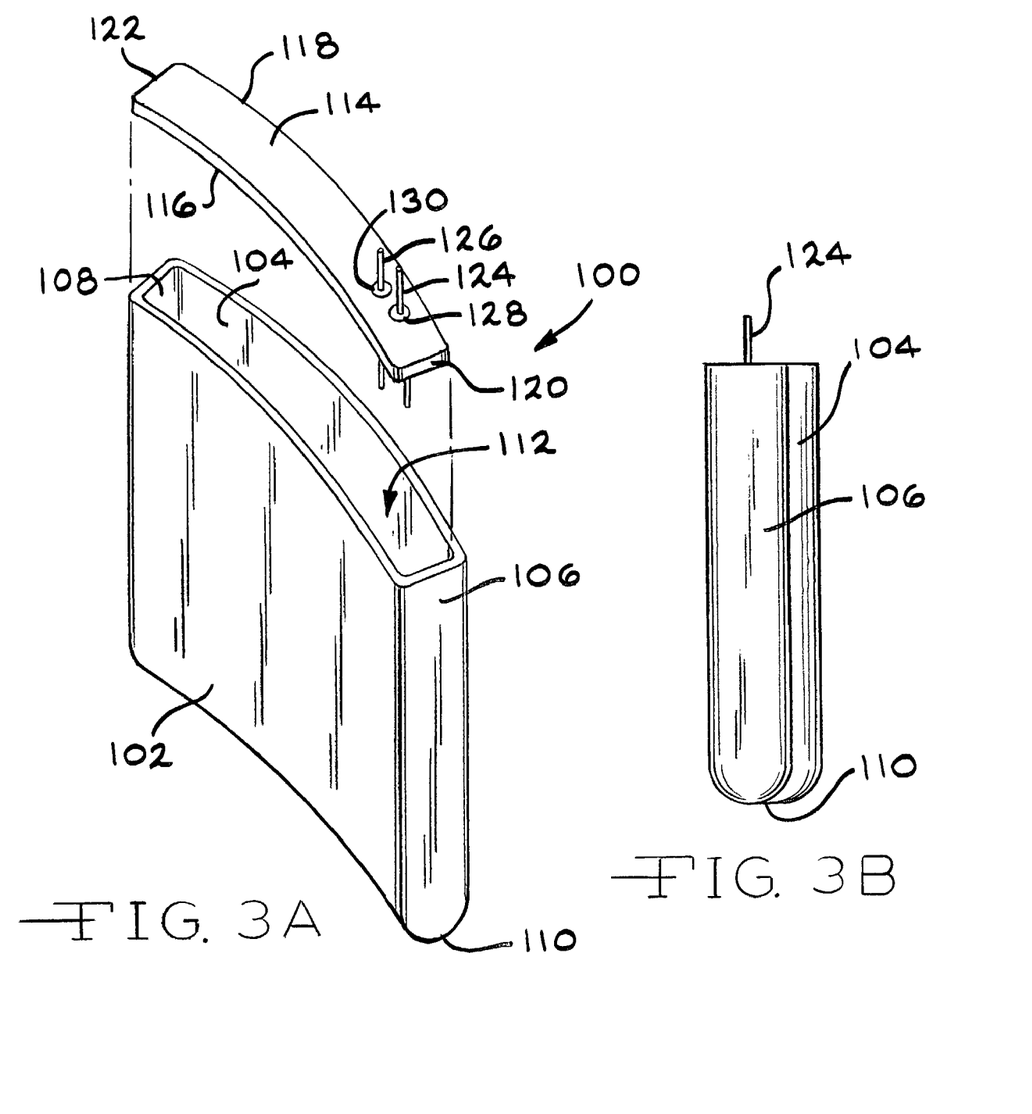
FIG. 3A is an exploded view of another embodiment of a contoured deep drawn cell housing 70 according to the present invention.
FIG. 3B is a side elevational view of the housing 70 shown in FIG. 3A.

FIGS. 3A and 3B illustrate another embodiment of a contoured deep drawing housing 100 including spaced apart and opposed major front and back side walls 102 and 104 extending to and meeting with planar right and left end walls 106 and 108. The side walls 102, 104 and end walls 106, 108 are connected to a curved bottom wall 110 forming the housing as a unitary, deep drawn member. Both of the major front and back side walls 102, 104 have a curved shape of a continuous radius deflecting in a similar direction and extending from the planar right and left end walls 106, 108. The curvatures of the front and back side walls 102, 104 are the same, however, as discussed with respect to housing 60, that is not necessary.

The side walls and end walls of the deep drawn housing 100 form an opening 112 closed by a generally planar lid 114. Lid 114 has a peripheral shape matching that of the opening 112 and formed of a concave edge 116 opposite a convex edge 118, both of which extend to and meet with straight right and left edges 120 and 122. That way, when the lid 114 is secured to the upper edges of the housing side walls and end walls, the opening 112 is closed.

As with the housing 60 of FIGS. 2A and 2B, the lid 114 includes feedthrough wires 124, 126 for connection to the body being assisted. The feedthrough wires 124, 126 are insulated from the lid 114 by respective glass or ceramic seals 128, 130.

Figure 4:
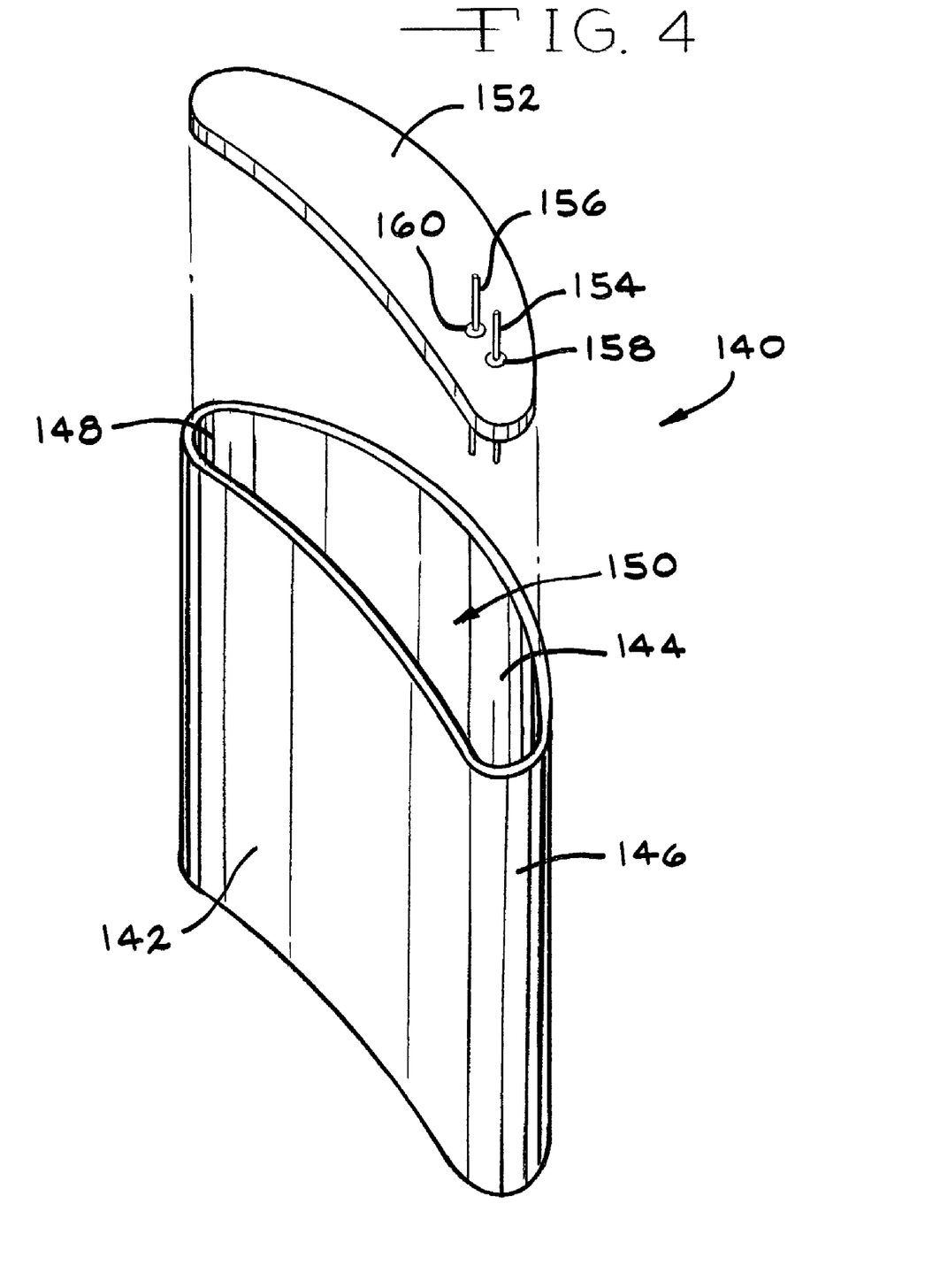
FIG. 4 is a perspective view of another embodiment of a contoured housing 270 according to the present invention having a front side wall 272 of a greater radial curvature than a back side wall 274.

FIG. 4 illustrates another embodiment of a contoured deep drawn housing 140 having spaced apart and opposed front and back side walls 142 and 144 extending to and meeting with curved right and left end walls 146 and 148. The side walls 142, 144 and end walls 146, 148 connect to a bottom wall (not shown) forming the housing as a unitary member. Both of the major front and back side walls 142, 144 have a curved shape of a continuous radius deflecting in a similar direction and extending from the end walls 146, 148. However, the curvature of front wall 142 is less than that of back wall 144. This means that the radius of the front wall 142 is greater than the radius of the back wall 144.

The side walls and end walls of the deep drawn housing 140 form an opening 150 closed by a lid 152. Lid 152 has a peripheral shape matching that of the opening 150. When the lid is secured to the upper edges of the housing, the opening 150 is closed in a hermetic manner. The lid also includes feedthrough wires 154, 156 for connection to the body being assisted. The feedthrough wires 154, 156 are insulated from the lid 152 by respective glass or ceramic seals 158, 160.

Figure 5:
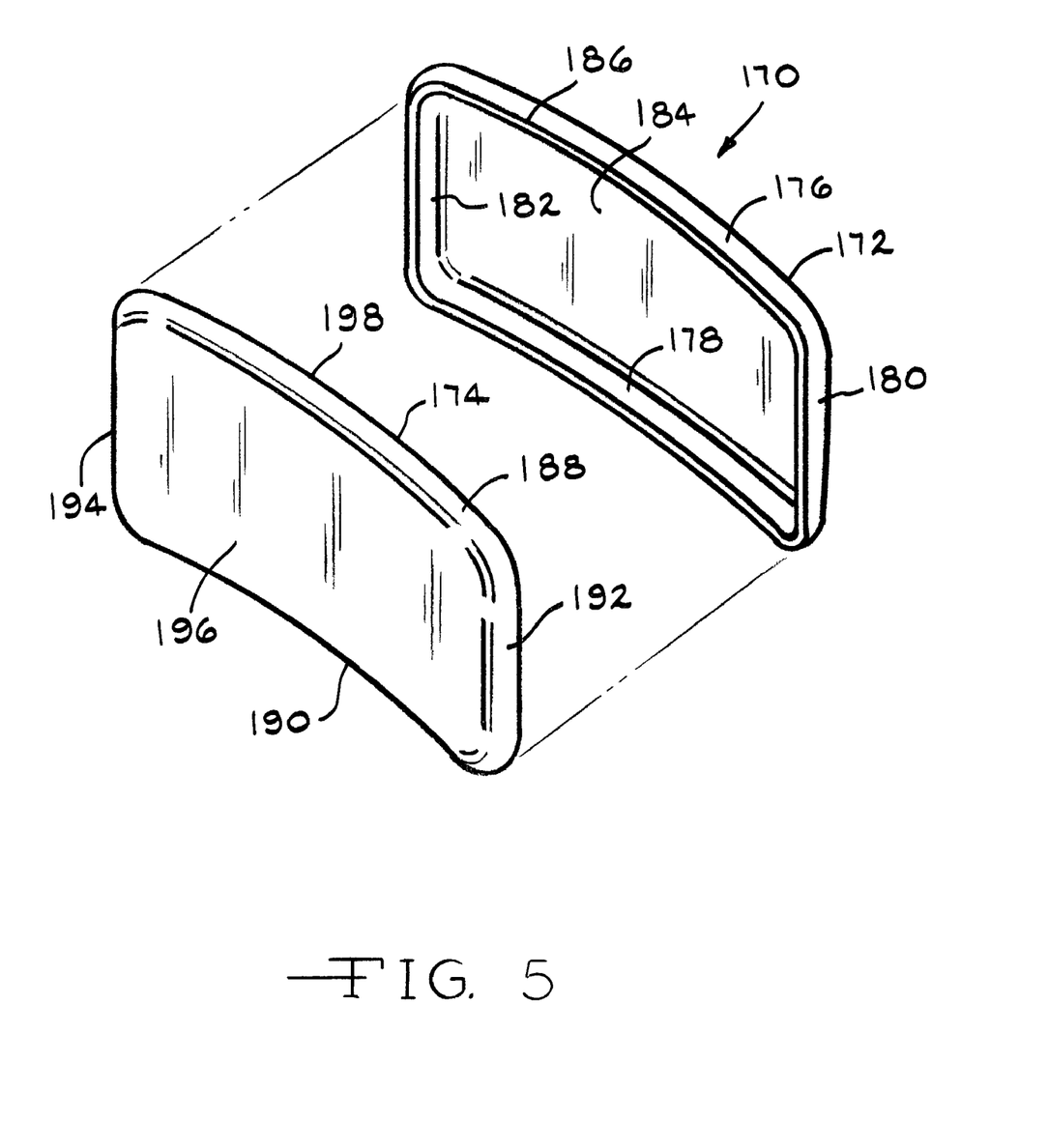
FIG. 5 is a perspective view of contoured clam shell housing portions 112 and 114 for another embodiment of a contoured housing 110.

FIG. 5 illustrates another embodiment of a contoured housing 170 according to the present invention. The housing has first and second clam shell portions 172 and 174 matable together and sealable about their periphery to provide a hermetic enclosure for an implantable medical device. The first clam shell 172 has a surrounding wall comprised of spaced apart side walls 176 and 178 extending to and meeting with spaced apart end walls 180 and 182. The side walls 176, 178 and the end walls 180, 182 meet at rounded corners and extend to a curved front wall 184 of a generally concave shape. Opposite the front wall 184 is a continuous edge 186 of the side walls 176, 178 and end walls 180, 182.

The second clam shell 174 has a surrounding wall comprised of spaced apart side walls 188 and 290 extending to and meeting with spaced apart end walls 192 and 194. The side walls 188 and 190 and end walls 192 and 194 meet at rounded corners and extend to a curved front wall 196 of a generally concave shape. Opposite the front wall is a continuous edge 198 of the side walls 188, 190 and end walls 192, 194.

The clam shells 172 and 174 are sized such that one of them has its side walls and end walls of a somewhat shorter length than those of the other. That way, after the components of the implantable device, including the power source and control circuitry, are nested in the one clam shell having the shorter side walls and end walls, the other clam shell is mated thereto. In this position, the shorter side walls and end walls are received in a closely spaced relationship partially covered by the somewhat longer side walls and end walls of the other clam shell. The one continuous edge 186, 198 of the larger clam shell is then secured to the side walls and end walls of the other clam shell, such as by welding. This provides a hermetic closure for the housing 170 having the major concave walls 184, 196 spaced from one another but of a similar curvature deflecting in a similar direction. Alternatively, one of the major concave walls 184, 196 can be of a greater curvature than the other or at least one of the major concave walls has at least first and second different curvatures, the first curvature transitioning into the second curvature. Also, one of the major walls 184, 196 can have at least a first and second different curvatures with a generally planar surface disposed between the curvatures. While not shown in the drawing, the housing includes insulated feedthroughs for connecting the device to the body part being assisted, in a similar manner as the previously described housings 34 (FIG. 1), 60 (FIGS. 2A and 2B), 100 (FIGS. 3A and 3B) and 140 (FIG. 4).

It is also within the scope of the present invention that the clam shells are butted together before they are sealed. This means that instead of the side walls and end walls of one of the clam shells being shorter than those of the other, they are of equal lengths. The butted edges are sealed together such as by welding.

Figure 6:
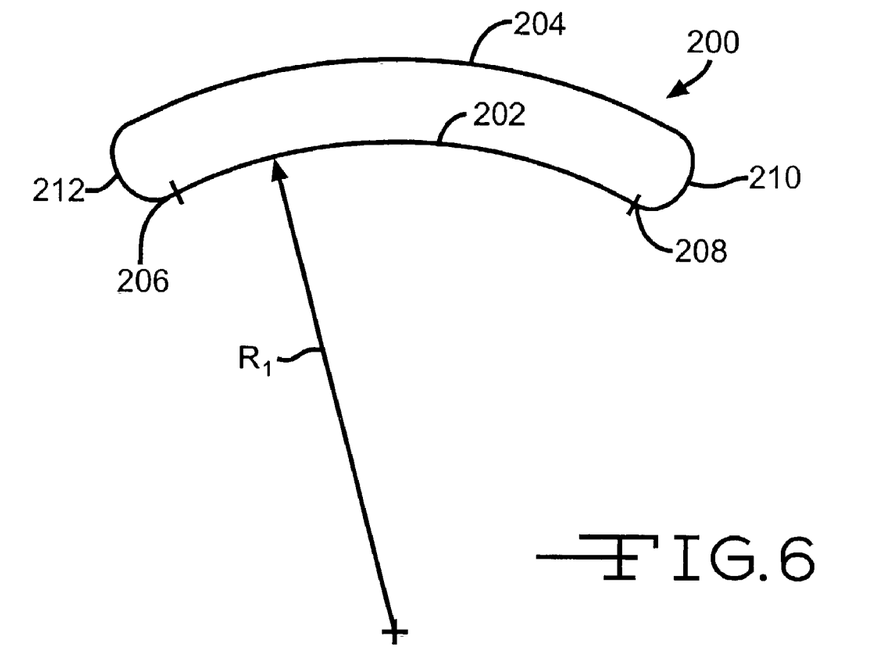
FIG. 6 is a schematic cross-sectional view of a housing having opposed major curved side walls of a radius R1.
Figure 7:
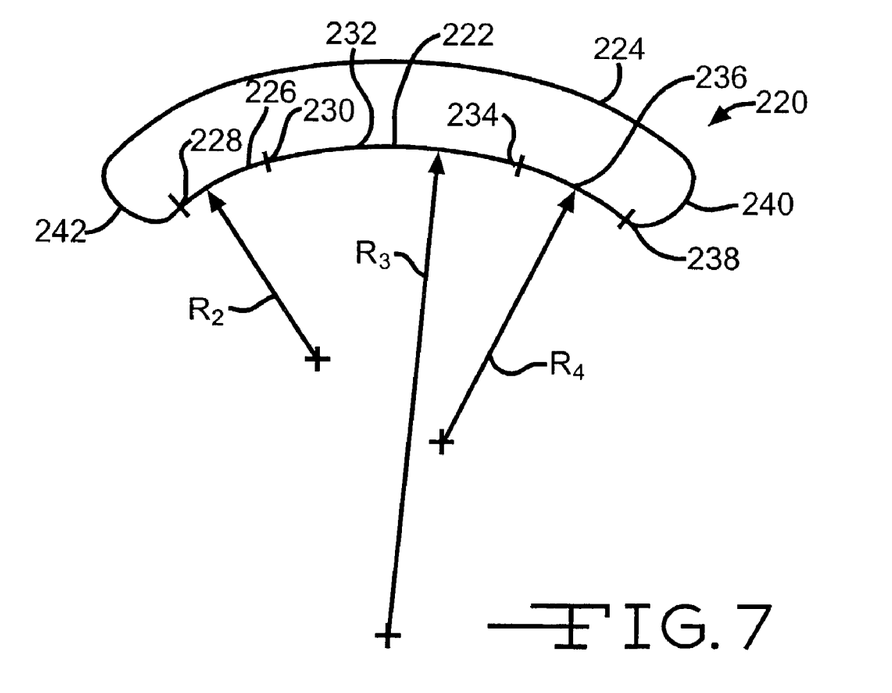
FIG. 7 is a schematic cross-sectional view of a housing having opposed major curved side walls of varying radii R2 to R4.
Figure 8:
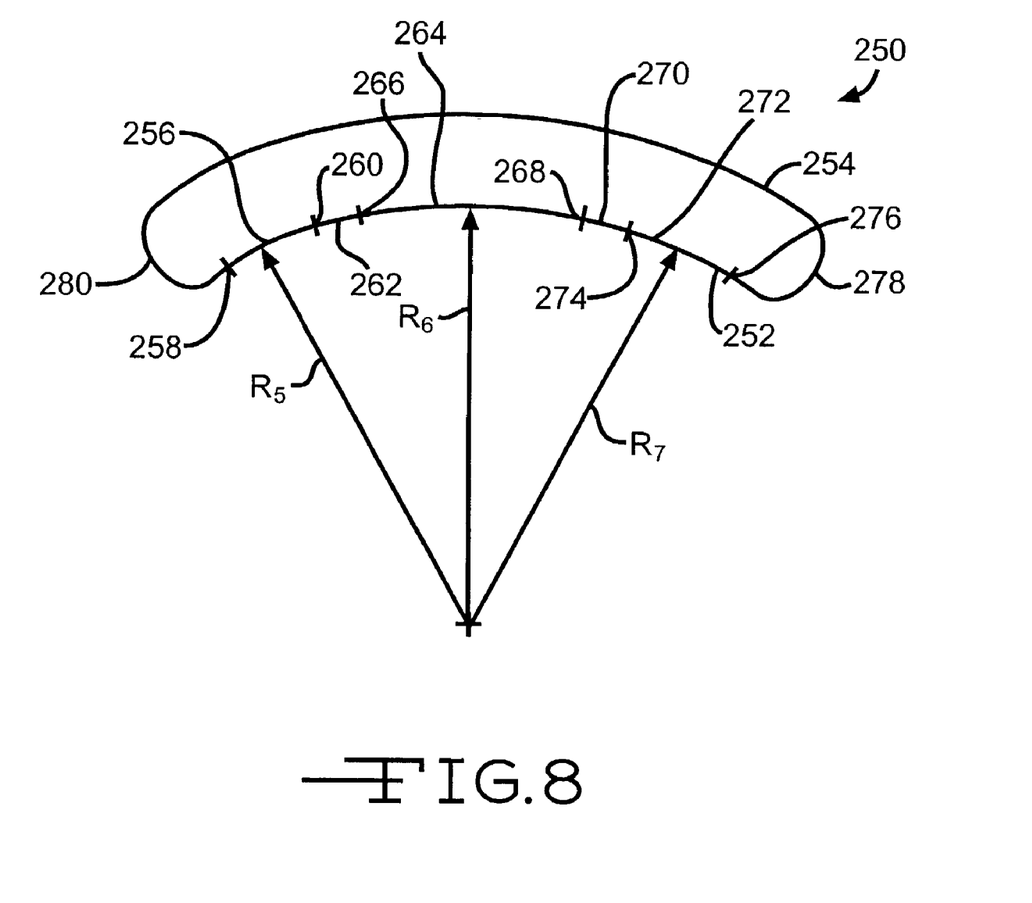
FIG. 8 is a schematic cross-sectional view of a housing having opposed major curved side walls of substantially equal radii R5 to R6 with intermediate planar sections.

Turning to FIGS. 6 to 8, these drawings show further representative schematic crosssectional views of deep drawn or clamshell housings having contoured or curved opposed major sidewalls according to the present invention. In FIG. 6, the housing 200 comprises spaced apart and opposed major first and second sidewalls 202 and 204. Sidewall 202 is of a curvature defined by the radius R1 moving along a path from tangent point 206 to tangent point 208. The radius R1 is not shown for the second sidewall 204, however, it is the same as that of the first side wall 202. The sidewalls 202, 204 extend to curved end walls 210 and 212 and a bottom wall (not shown). The housing 200 is then hermetically closed by a lid (not shown).

FIG. 7 shows another embodiment of a housing 220 comprising spaced apart and opposed major first and second curved side walls 222 and 224. The first major side wall 222 is comprised of a first curved portion 226 defined by radius R2 moving along a path from tangent point 228 to tangent point 230 where the side wall transitions to a second curved portion 232 defined by radius R2 moving along a path from tangent point 230 to tangent point 234. At tangent point 234, the second curved portion 232 transitions to a third curved portion 236 defined by radius R3 moving along a path from tangent point 234 to tangent point 238.

As the drawing shows, the length of the radius R2 is less than that of both R3 and R4 while the length of radius R4 is less than that of R3. The second major side wall 224 is similar in its contoured or curved shape. The side walls 222 and 224 extend to curved end walls 240 and 242 and a bottom wall (not shown). The housing 220 is then heremetically closed by a lid (not shown).

It is within the scope of the present invention that the arrangement of the respective curved portions 226, 232 and 236 can be rearranged in any sequence or manner. Also, there can be only two different curved portions in a side wall or more than three. The exact number and their arrangement is only limited by the parameters of the particular application in which the implantable device cell will be used.

FIG. 8 shows another embodiment of a housing 250 comprising spaced apart and opposed major first and second curved side walls 252 and 254 according to the present invention. The first major side wall 252 is comprised of a first curved portion 256 defined by radius R5 moving along a path from tangent point 258 to tangent point 260 where the side wall transitions to a first planar or straight portion 262. The first planar portion 262 then transitions to a second curved portion 264 defined by radius R6 moving along a path from tangent point 266 to tangent point 268. At tangent point 268, the side wall 252 transitions to a second planar portion 270 which, in turn, transitions to a third curved portion 272 defined by radius R7 moving along a path from tangent point 274 to tangent point 276.

As the drawing shows, the lengths of radii R5, R6 and R7 are substantially equal. However, as described above with respect to FIG. 7, that is not necessary. The lengths of planar portions 262 and 270 are equal, however, that is also not necessary. There can be more or less than two planar portions in a side wall and they can be continuous and angled with respect to each other or separated from each other by one or more curved portions.

Again, the second major side wall 254 is similar in shape to the first side wall 252. The side walls 252 and 254 extend to curved end walls 278 and 280 and a bottom wall (not shown). The housing 250 is then hermetically closed by a lid (not shown).

It is appreciated that various modifications to the present inventive concepts described herein may be apparent to those of ordinary skill in the art without departing from the spirit and scope of the present invention as defined by the herein appended claims.

What is claimed is:

1. A method for providing an implantable medical device, comprising the steps of:

a) providing a first metal housing member having a first major side wall extending to and meeting with a first surrounding side wall;

b) providing a second metal housing member having a second major side wall extending to and meeting with a second surrounding side wall;

c) nesting an electrical energy power source and a control circuitry inside one of the first and second housing members, the electrical energy power source for powering the control circuitry;

d) connecting the control circuitry to a feedthrough supported in one of the first and second housing members; and e) sealing the other of the first and second housing members to the one of the first and the second housing members in a hermetic manner with a first edge of the first surrounding side wall facing the second major side wall and a second edge of the second surrounding side wall facing the first major side wall, wherein a portion of one of the first and second surrounding sidewalls is in a partially overlapping relationship with the other of the surrounding sidewalls and wherein the one of the first and second edges is hermetically secured to the other of the first and second surrounding sidewalls with the housing having the first and second major sidewalls deflecting in a similar direction.

2. The method of claim 1 including providing the first and second major side walls of the respective first and second housing members being continuously curved.

3. The method of claim 1 including providing the first major sidewall of the first housing member having a greater curvature than the second major sidewall of the second housing member.

4. The method of claim 1 including providing at least one of the first and the second major sidewalls of the respective first and second housing members comprising at least a first and second different curvatures, the first curvature transitioning into the second curvature.

5. The method of claim 1 including providing at least one of the first and the second major sidewalls of the respective first and second housing members comprising at least a first and a second different curvatures with a generally planar surface disposed between the first curvature and the second curvature.

6. A method for providing an implantable medical device, comprising the steps of:
   a) providing a housing comprising a deep drawn metal casing comprising spaced apart first and second major side walls extending to and meeting with opposed third and fourth end walls, the major sidewalls and end walls extending from an opening to a bottom wall, wherein the first and second major side walls are curved to deflect in a similar direction where they connect to the third end wall and where they connect to the fourth end wall, wherein the spaced apart first and second major sidewalls and the opposed third and fourth end walls are at their maximum distance from each other at the opening;
   b) housing an electrical energy power source and a control circuitry inside the housing through the opening, the electrical energy power source for powering the control circuitry;
   c) connecting the control circuitry to a feedthrough supported in a lid for the housing; and
   d) sealing the opening with the lid.

7. The method of claim 6 including providing the first and second major side walls being continuously curved from their connection to the third end wall to their connection to the opposed fourth end wall.

8. The method of claim 6 including providing the first major sidewall of a greater curvature than the second major sidewall.

9. The method of claim 6 including providing at least one of the first and second major side walls of at least a first and a second different curvatures, the first curvature transitioning into the second curvature.

10. The method of claim 6 including providing at least one of the first and second major side walls of at least a first and a second different curvatures with a generally planar surface disposed between the first curvature and the second curvature.

11. A method for providing an implantable medical device, comprising the steps of:
   a) providing a housing comprising a deep drawn metal casing comprising spaced apart first and second major sidewalls extending to and meeting with an intermediate wall having a generally radius curved shape, wherein the first and second major sidewalls are curved to deflect in a similar direction where they meet the intermediate wall and wherein the spaced apart first and second major sidewalls and opposed portions of the intermediate wall where it meets the major sidewalls at an opening are at their maximum distance from each other at the opening;
   b) housing an electrical energy power source and a control circuitry inside the housing through the opening, the electrical energy power source for powering the control circuitry;
   c) connecting the control circuitry to a feedthrough supported in a lid for the housing; and
   d) sealing the opening with a lid.

12. The method of claim 11 including providing the first and second major sidewalls of a continuous curvature.

13. The method of claim 11 including providing at least one of the first and the second major side walls of at least a first and a second different curvatures, the first curvature transitioning into the second curvature.

14. The method of claim 11 including providing at least one of the first and second major side walls of at least a first and a second different curvatures with a generally planar surface disposed between the first curvature and the second curvature.

15. The method of claim 11 including providing the first major sidewall of a greater curvature than the second major sidewall.

16. An implantable medical device, which comprise:
   a) an electrical energy storage device;
   b) a control circuitry; and
   c) a housing for the power source and the control circuitry, wherein the housing comprises a deep drawn metal casing comprising spaced apart first and second major side walls extending to and meeting with opposed third and fourth end walls, the major sidewalls and end walls extending from an opening closed by a metal lid to a bottom wall, and wherein the first and second major side walls are curved to deflect in a similar direction where they connect to the third end wall and where they connect to the fourth end wall, wherein the spaced apart first and second major sidewalls and the opposed third and fourth end walls are at their maximum distance from each other at the opening closed by the lid.

17. The implantable medical device of claim 16 wherein the first and second major sidewalls are continuously curved from their connection to the third end wall to their connection to the opposed fourth end wall.

18. The implantable medical device of claim 17 wherein the first major sidewall is of a greater curvature than the second major sidewall.

19. The implantable medical device of claim 16 wherein at least one of the first and second major sidewalls is of at least a first and a second different curvatures, the first curvature transitioning into the second curvature.

20. The implantable medical device of claim 16 wherein at least one of the first and second major sidewalls is of at least a first and a second different curvatures with a generally planar surface disposed between the first curvature and the second curvature.

21. The implantable medical device of claims 16 wherein the third and fourth end walls are curved.

22. The implantable medical device of claim 16 wherein the third and fourth end walls are generally planar.

23. The implantable medical device of claim 1 wherein the lid supports at least one feedthrough pin.

24. The implantable medical device of claim 16 selected from the group consisting of a hearing-assist device, a neurostimulator, a cardiac pacemaker, a cardiac defibrillator, a heart-assist device and a drug pump.

25. The implantable medical device of claim 16 wherein the housing is of a material selected from the group consisting of nickel, aluminum, stainless steel, mild steel, tantalum and titanium.

26. An implantable medical device, which comprise:
   a) an electrical energy storage device;
   b) a control circuitry; and
   c) a housing for the power source and the control circuitry, wherein the housing comprises a deep drawn metal casing comprising spaced apart first and second major side walls extending to and meeting with an intermediate wall having a generally radius curved shape, wherein the intermediate wall comprises opposed intermediate wall portions meeting the first and second major side walls at an opening and wherein the first and second major side walls are curved to deflect in a similar direction where each of them meets the opposed intermediate wall portions, wherein the spaced apart first and second major sidewalls meeting the opposed intermediate wall portions are at their maximum distance from each other at the opening closed by a lid.

27. The implantable medical device of claim 26 wherein the first and second major sidewalls are of a continuous curvature.

28. The implantable medical device of claim 26 wherein at least one of the first and second major sidewalls is of at least a first and a second different curvatures, the first curvature transitioning with the second curvature.

29. The implantable medical device of claim 26 wherein at least one of the first and second major sidewalls is of at least a first and a second different curvatures with a generally planar surface disposed between the first curvature and the second curvature.

30. The implantable medical device of claim 26 wherein the first major sidewall is of a greater curvature than the second major sidewall.

31. The implantable medical device of claim 26 wherein the lid supports at least one feedthrough pin.

32. An implantable medical device, which comprises:
    a) an electrical energy storage device;
    b) a control circuitry;
    c) a housing for the power source and the control circuitry, wherein the housing comprises a first metal member having a first major side wall extending to and meeting with a first surrounding side wall and a second metal member having a second major side wall extending to and meeting with a second surrounding side wall to provide the housing having the first and second major sidewalls deflecting in a similar direction and wherein a first edge of the first surrounding side wall faces the second major side wall and a second edge of the second surrounding side wall faces the first major side wall with a portion of the first surrounding side wall in an overlapping relationship with a portion of the second surrounding side wall having the first edge hermetically secured to the second surrounding sidewall.

33. The implantable medical device of claim 32 wherein the first and second major sidewalls are continuously curved.

34. The implantable medical device of claim 32 wherein the first major sidewall is of a greater curvature than the second major sidewall.

35. The implantable medical device of claim 32 wherein at least one of the first and second major sidewalls is of at least a first and second different curvatures, the first curvature transitioning into the second curvature.

36. The implantable medical device of claim 32 wherein at least one of the first and second major sidewalls is of at least a first and a second different curvatures with a generally planar surface disposed between the first curvature and the second curvature.

37. A housing for an implantable medical device, the housing comprising:
    a) a deep drawn metal casing comprising spaced apart first and second major side walls extending to and meeting with opposed third and fourth end walls, the major sidewalls and end walls extending from an opening to a bottom wall, wherein the first and second major side walls are curved to deflect in a similar direction where they connect to the third end wall and where they connect to the fourth end wall; and
    b) a lid, wherein the spaced apart first and second major sidewalls and the opposed third and fourth end walls are at their maximum distance from each other at the opening closed by the lid.

38. The housing of claim 37 wherein the first and second major sidewalls are each curved from their connection to the third end wall to their connection to the opposed fourth end wall.

39. The housing of claim 37 wherein the first sidewall is of a greater curvature than the second major sidewall.

40. The housing of claim 37 wherein the third and fourth end walls are curved.

41. The housing of claim 37 wherein the third and fourth end walls are curved opposite each other.

42. A housing for an implantable medical device, the housing comprising:
    a) a deep drawn metal casing comprising spaced apart first and second major side walls extending to and meeting with an intermediate wall having a generally radius curved shape and a bottom wall, wherein the first and second major side walls are curved to deflect in a similar direction where they meet the intermediate wall, wherein the spaced apart first and second major sidewalls and opposed portions of the intermediate wall where it meets the major sidewalls at an opening of the housing are at their maximum distance from each other at the opening; and
    b) a lid closing the opening.

43. The housing of claim 42 wherein the first and second major sidewalls are of a continuous curvature.

44. The housing of claim 42 wherein at least one of the first and second major side walls is of at least a first and a second different curvatures, the first curvature transitioning with the second curvatures.

45. The housing of claim 42 wherein at least one of the first and second major side walls is of at least a first and a second different curvatures with a generally planar surface disposed between the first curvature and the second curvature.

46. The housing of claim 42 wherein the first major sidewall is of a greater curvature than the second major sidewall.

47. The housing of claim 46 wherein the housing is of a material selected from the group consisting of nickel, aluminum, stainless steel, mild steel, tantalum and titanium.

48. A housing for an implantable medical device, the housing comprising:
    a) a first metal member having a first major side wall extending to and meeting with a first surrounding side wall; and
    b) a second metal member having a second major side wall extending to and meeting with a second surrounding side wall, wherein a first edge of the first surrounding side wall faces the second major side wall and a second edge of the second surrounding side wall faces the first major side wall, and wherein a portion of the first surrounding side wall overlaps a portion of the second surrounding side wall, the first edge being hermetically secured to the second surrounding sidewall with the housing having the first and second major sidewalls deflecting in a similar direction.

49. The housing of claim 48 wherein the first and second major sidewalls are continuously curved.

50. The housing of claim 48 wherein the first major side wall is of a greater curvature than the second major side wall.

51. The housing of claim 48 wherein at least one of the first and second major side walls is of at least a first and second different curvatures, the first curvature transitioning into the second curvature.

52. The housing of claim 48 wherein at least one of the first and second major side walls is of at least a first and a second different curvatures with a generally planar surface disposed between the first curvature and the second curvature.

* * * * *